United States Patent
Ahlgren et al.

(10) Patent No.: US 8,505,121 B2
(45) Date of Patent: Aug. 13, 2013

(54) HEAD SUSPENSION HAVING TRANSITION ARMS AND REAR SUPPORT

(75) Inventors: Lars-Olov Ahlgren, Fellingsbro (SE); Niklas M. S. Lilenthal, Leksand (SE); Arne O. Linderstrand, Leksand (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/590,766

(22) Filed: Aug. 21, 2012

(65) Prior Publication Data

US 2012/0311752 A1    Dec. 13, 2012

Related U.S. Application Data

(62) Division of application No. 12/681,829, filed as application No. PCT/US2008/078657 on Oct. 3, 2008.

(60) Provisional application No. 60/978,824, filed on Oct. 10, 2007.

(51) Int. Cl.
*A42B 1/22* (2006.01)

(52) U.S. Cl.
USPC ........................................ 2/417; 2/418; 2/420

(58) Field of Classification Search
USPC ............................................. 2/416–421, 8.2
See application file for complete search history.

(56) References Cited

U.S. PATENT DOCUMENTS

| | | | |
|---|---|---|---|
| 2,187,932 A | 1/1940 | Roe | |
| 2,272,833 A | 2/1942 | Dockson | |
| 2,360,482 A | 10/1944 | Evans | |
| 2,679,046 A * | 5/1954 | Dye | 2/416 |
| 2,763,006 A | 9/1956 | Amundsen | |
| 2,769,176 A | 11/1956 | Grancsay | |
| 2,814,043 A | 11/1957 | Alesi | |
| 3,047,876 A | 8/1962 | Malcom | |
| 3,354,468 A | 11/1967 | Bowers | |
| 3,388,405 A | 6/1968 | Simpson | |
| 3,500,474 A | 3/1970 | Austin | |
| 3,591,863 A | 7/1971 | Rickard | |
| 3,696,440 A * | 10/1972 | Littleton | 2/418 |
| 3,696,442 A | 10/1972 | Amundsen | |
| 3,763,495 A | 10/1973 | DeAngelis | |
| 3,852,821 A | 12/1974 | Mickel | |
| 3,866,244 A | 2/1975 | Ruck | |
| 3,866,727 A | 2/1975 | Myers | |
| 3,906,548 A * | 9/1975 | Kallis | 2/181.4 |
| 4,000,520 A | 1/1977 | Svendsen | |
| 4,263,679 A | 4/1981 | Erlendson | |
| 4,463,456 A * | 8/1984 | Hanson | 2/416 |
| 4,888,831 A * | 12/1989 | Oleson | 2/420 |

(Continued)

FOREIGN PATENT DOCUMENTS

| | | |
|---|---|---|
| EP | 1 386 950 | 2/2004 |
| EP | 1 835 003 | 9/2007 |
| WO | 2005/019367 | 3/2005 |

*Primary Examiner* — Khoa Huynh
*Assistant Examiner* — Andrew W Collins
(74) *Attorney, Agent, or Firm* — Kenneth B. Wood

(57) ABSTRACT

A head suspension includes a headband portion having a length and two transition arms. Each transition arm is coupled to the headband portion and extends away from the headband portion length at an angle greater than zero degrees. Each transition arm has a distal end and a pivot at the distal end. The pivot characterized by a pivot point and a rear support portion is pivotally connected to each pivot.

17 Claims, 6 Drawing Sheets

(56) References Cited

U.S. PATENT DOCUMENTS

| | | | |
|---|---|---|---|
| 4,942,628 A | 7/1990 | Freund | |
| 4,986,282 A | 1/1991 | Stackhouse | |
| 5,044,019 A | 9/1991 | Shewchenko | |
| 5,077,836 A | 1/1992 | Idoff | |
| 5,191,468 A | 3/1993 | Mases | |
| 5,421,799 A | 6/1995 | Rabin | |
| 5,571,217 A | 11/1996 | Bovin | |
| 5,572,749 A | 11/1996 | Ogden | |
| 5,592,936 A | 1/1997 | Thomas | |
| 5,619,754 A | 4/1997 | Thurwanger | |
| 5,845,341 A | 12/1998 | Barhold | |
| 5,896,586 A | 4/1999 | Freund | |
| 6,314,588 B1 | 11/2001 | Fang | |
| 6,341,382 B1 | 1/2002 | Ryvin | |
| 6,393,617 B1 | 5/2002 | Paris | |
| 6,481,025 B2 | 11/2002 | Hill | |
| 6,711,748 B2 | 3/2004 | Paris | |
| 6,751,811 B1 | 6/2004 | Hill | |
| 6,862,747 B2 | 3/2005 | Oleson | |
| 6,990,691 B2 | 1/2006 | Klotz | |
| 7,007,306 B2 | 3/2006 | Howard | |
| 7,043,772 B2 * | 5/2006 | Bielefeld et al. | 2/418 |
| 7,114,197 B2 | 10/2006 | Garneau | |
| 7,120,939 B1 | 10/2006 | Howard | |
| 7,770,239 B1 * | 8/2010 | Goldman et al. | 2/416 |
| 2006/0185052 A1 | 8/2006 | Huh | |
| 2012/0144565 A1 * | 6/2012 | Huh | 2/421 |

\* cited by examiner

HEAD SUSPENSION HAVING TRANSITION ARMS AND REAR SUPPORT

CROSS-REFERENCE TO RELATED APPLICATIONS

The present patent application is a divisional of U.S. patent application Ser. No. 12/681,829, having a filing date of Oct. 3, 2008 from International Application PCT/US2008/078657, which claims priority to U.S. Provisional Patent Application No. 60/978,824, filed on Oct. 10, 2007.

FIELD

The present disclosure relates to a head suspension for protective headgear and particularly to a head suspension having transition arms and a rear support portion pivotally connected to the transition arms.

BACKGROUND

Protective headgear, for example construction hard hats, helmets, such as fire fighter helmets, shields such as welding shields and grinding shields, sports equipment headgear, and the like often include a headgear support or head suspension. The heargear supports or head suspension often include with headbands and/or head straps that are adjustable so that the headgear can be supported comfortably on any size head by the headband.

In many headgear supports or head suspensions, it is desired that the headband be easy to adjust and that it fit adequately without discomfort to the user. In some cases, it is also desired that headgear supports or head suspension headbands do not require that the headgear be removed from the user's head in order to make adjustments in the size of the head suspension. Furthermore, it is desired that the head suspension be comfortable to wear for extended periods of time without excessive need of re-positioning or adjustments. Accordingly, there is a need for head suspensions that are more comfortable to wear for longer periods of time and that are easier to adjust.

BRIEF SUMMARY

The present disclosure relates to a head suspension for protective headgear and particularly to a head suspension having transition arms and a rear support portion pivotally connected to the transition arms.

In a first embodiment, a head suspension includes a headband portion having a length and two transition arms. Each transition arm is coupled to the headband portion and extends away from the headband portion length at an angle greater than zero degrees. Each transition arm has a distal end and a pivot at the distal end. The pivot characterized by a pivot point and a rear support portion is pivotally connected to each pivot.

In another embodiment, a head suspension includes a laterally extending headband portion having a length and two transition arms. Each transition arm is coupled to the headband portion and extends longitudinally away from the headband portion length. Each transition arm has a distal end and a pivot at the distal end. The pivot characterized by a pivot point and a rear support portion is pivotally connected to each pivot.

In a further embodiment, a head protection device includes a laterally extending headband portion having a length and two transition arms. Each transition arm is coupled to the headband portion and extends longitudinally away from the headband portion length. Each transition arm has a distal end and a pivot at the distal end. The pivot characterized by a pivot point. A rear support portion is pivotally connected to each pivot. A head protection element is attached to the head suspension.

BRIEF DESCRIPTION OF THE DRAWINGS

The invention may be more completely understood in consideration of the following detailed description of various embodiments of the invention in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying drawings that form a part hereof, and in which are shown by way of illustration several specific embodiments. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure relates to a head suspension for protective headgear and particularly to a head suspension having transition arms and a rear support portion pivotally connected to the transition arms. The disclosed head suspension is comfortable to wear for prolonged periods of time and reduce the need for the user to re-position or adjust the headgear supports or head suspension headband during use, and at the same time is suitable for carrying a head protection element. The rear support portion is pivotally coupled low on the user's head so that the position of the rear support portion avoids certain pressure points on the back of the user's head. While the present invention is not so limited, an appreciation of various aspects of the invention will be gained through a discussion of the examples provided below.

Figure 1:
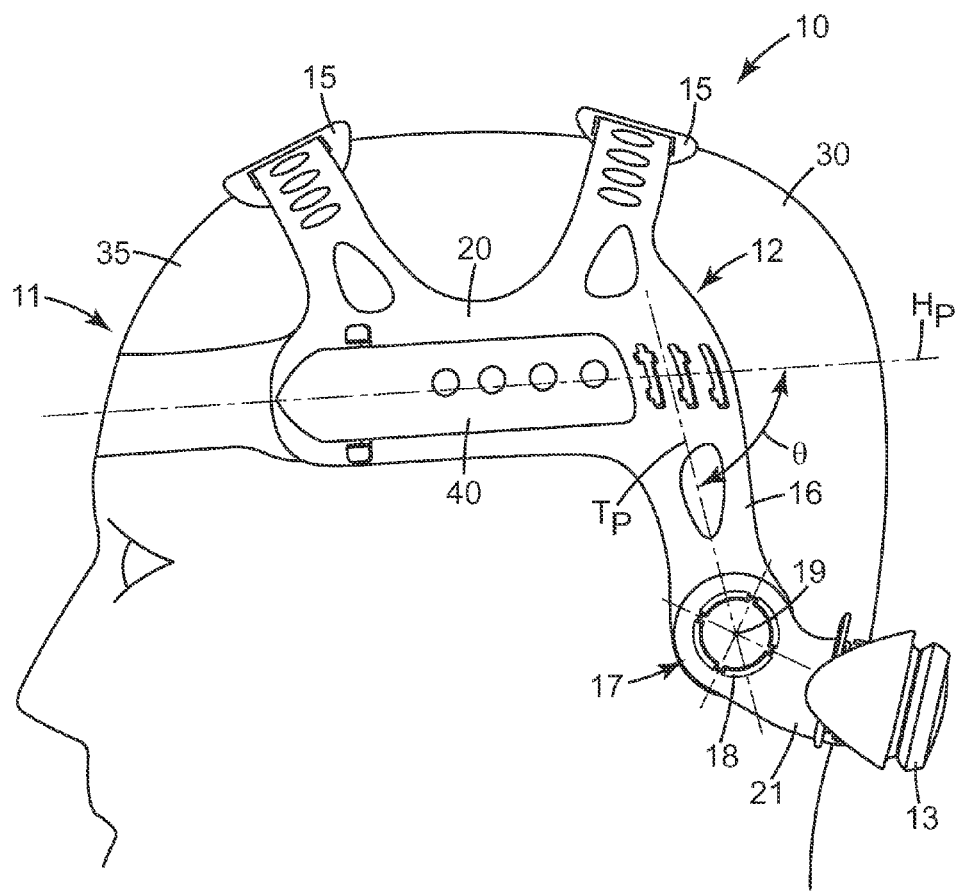
FIG. 1 is a schematic side view of an illustrative head suspension.
Figure 2:
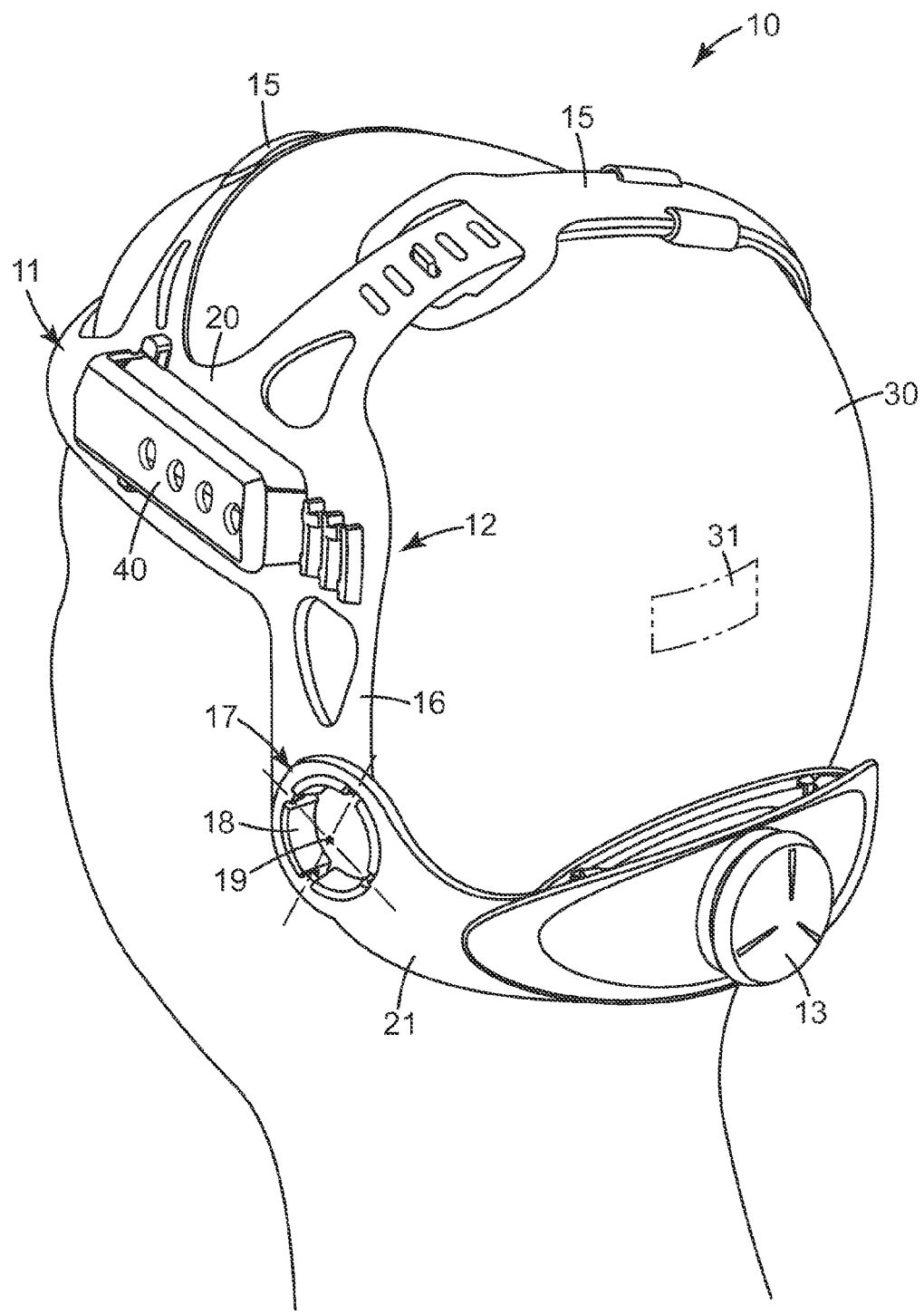
FIG. 2 is a schematic perspective rear view of the illustrative head suspension shown in FIG. 1.
Figure 3:
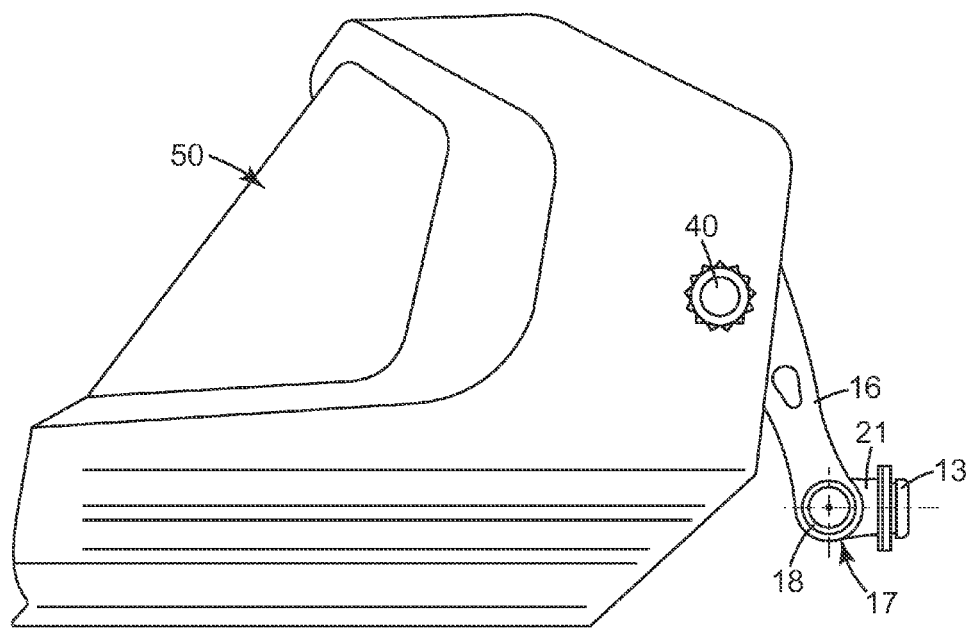
FIG. 3 is a schematic side elevation view of an illustrative head protection element.
Figure 4:
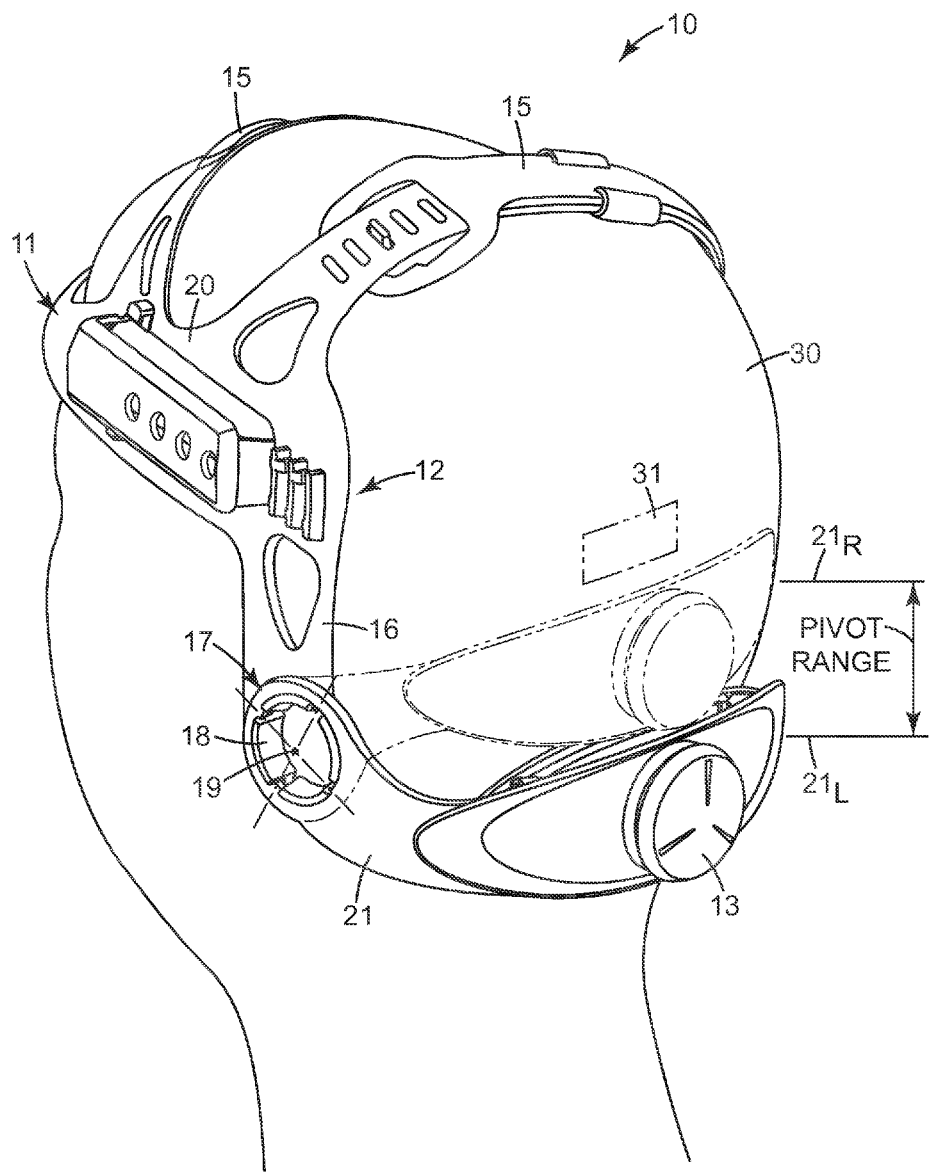
FIG. 4 is a schematic rear perspective view of an illustrative head suspension.
Figure 5:
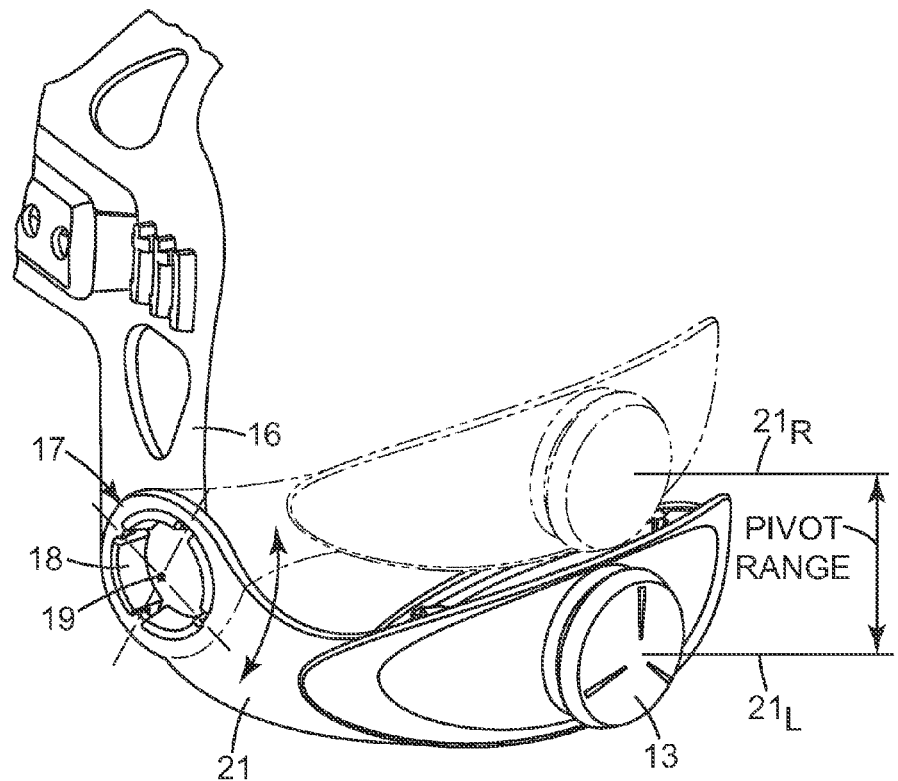
FIG. 5 is a schematic perspective view of an illustrative rear support portion.

FIG. 1 is a schematic side view of an illustrative head suspension 10. FIG. 2 is a schematic perspective rear view of the illustrative head suspension 10 shown in FIG. 1. FIG. 3 is a schematic side elevation view of an illustrative head protection element 50. FIG. 4 is a schematic rear perspective view of an illustrative head suspension 10. FIG. 5 is a schematic perspective view of an illustrative rear support portion 21.

The head suspension 10 includes a headband 20 that extends about a user's head 30. The head suspension 10 includes one or more top bands 15 that extend over the user's head 30 and each end of the top bands is joined to the headband 20. The head suspension 10 includes a head protection attachment element 40.

The head protection attachment element 40 couples a head protection element to the head suspension 10. In many embodiments, the head protection attachment element 40 pivotally couples a head protection element 50 to the head suspension 10 allowing the head protection element 50 to pivot relative to the head suspension 10. The head protection element 50 can be any useful head protection element such as, for example, a welding helmet or shield, a hard hat, a fire fighter helmet, a grinding shield, sports equipment headgear, and the like.

The headband 20 is an elongated element having a band length and includes a front portion 11 and a rear portion 12. The headband 20 has a length and two transition arms 16. Each transition arm 16 is coupled to the headband 20 at or near the rear portion 12. A proximal end of each transition arm 16 is coupled to the headband 20 by any suitable coupling means, such as permanent or removable mechanical attachment means. In one exemplary embodiment, as illustrated, transition arms 16 may be formed integrally with the headband 20. In another embodiment, transition arms 16 may be pivotally coupled with the headband 20. Each transition arm can have any useful length defined by a linear distance between the proximal end to a distal end 17. One example of this length is defined by the linear distance between a bottom edge of the headband 20 and the pivot point 19. This length can be, for example, in a range from 1 to 15 cm, or in a range from 2 to 10 cm, or in a range from 2 to 6 cm.

Each transition arm 16 extends away from the headband 20 length at an angle θ greater than zero degrees, or, in some exemplary embodiments, from 20 to 110 degrees, or from 60 to 110 degrees, or from 60 to 90 degrees. Each transition arm 16 has a distal end 17 and a pivot 18 at the distal end 17. The pivot 18 is characterized by a pivot point 19, which corresponds to a center of rotation of an adjacent portion of the rear support portion 21 with respect to a transition arm 16 it is pivotally connected to. A rear support portion 21 is pivotally connected to each pivot 18.

The rear support portion 21 can include an adjustment element 13 configured to adjust a head size of the head suspension 10. One exemplary adjustment element 13 is an adjustment knob providing a ratchet-type head size adjustment as described in U.S. Pat. No. 4,942,628, and incorporated by reference herein to the extent is does not conflict with the present disclosure. However, any other types of adjustments that enable a user to tighten and/or loosen the head suspension 10 about a users head are within the scope of the present disclosure.

The headband 20 front portion 11 is configured to be disposed across a forehead 35 of a user 30. The headband 20 length extends along a headband plane $H_P$ (a plane extending into the paper and through the top of the head 30 and across a forehead 35 of a wearer). A front major surface of the transition arm 16 may be used to define a transition arm axis $T_P$. The transition arm axis $T_P$ is a straight line extending generally along the length direction the transition arm 16 and extending through the central region of the transition arm 16. The intersection of the headband plane $H_P$ and the transition arm axis $T_P$ forms an angle θ having the value ranges described above. In many embodiments, the headband 20 extends laterally about the user's head 30 and the transition arms 16 extend generally longitudinally relative to the laterally extending headband 20.

In many embodiments, the headband portion 20 is configured to be disposed against the forehead 35 of the user 30 and the rear support 21 is configured to be disposed at or below an occipital bone region of a user. In some embodiments, the headband portion 20 is further configured to be disposed against the forehead 35 of the user 30 and the rear support 21 is configured to be disposed in line with an ear canal (i.e., external acoustic meatus) of the user and below the ear canal (i.e., external acoustic meatus) of the user. In some embodiments, the headband portion 20 is configured to be disposed against the forehead 35 of the user 30 and the rear support 21 is configured to be disposed at or below a transverse occipital suture and/or an external occipital protuberance of a user's skull.

In other embodiments, the headband portion 20 is configured to be disposed against the forehead 35 of a user 30 and each pivot point 19 is configured to be disposed below a BL-9 and GB-19 skull pressure points 31 of the user. In some embodiments, the headband portion 20 is configured to be disposed against the forehead 35 of the user 30 and the rear support 21 is configured to be disposed below a BL-9 and GB-19 skull pressure points 31 of the user. In some exemplary embodiments, the ends of the rear support 21 can be pivoted about the pivot points 19 to move through a PIVOT RANGE defined by a rear support 21 raised position $21_R$ and a rear support 21 lowered position $21_L$.

Figure 6:
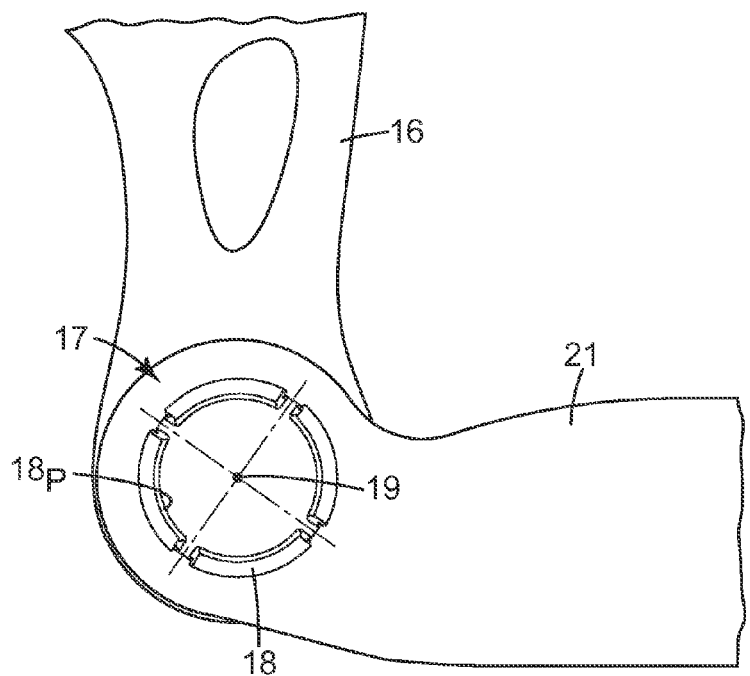
FIG. 6 is a schematic side elevation view of an illustrative rear support portion and transition arm pivot connection.
Figure 7:
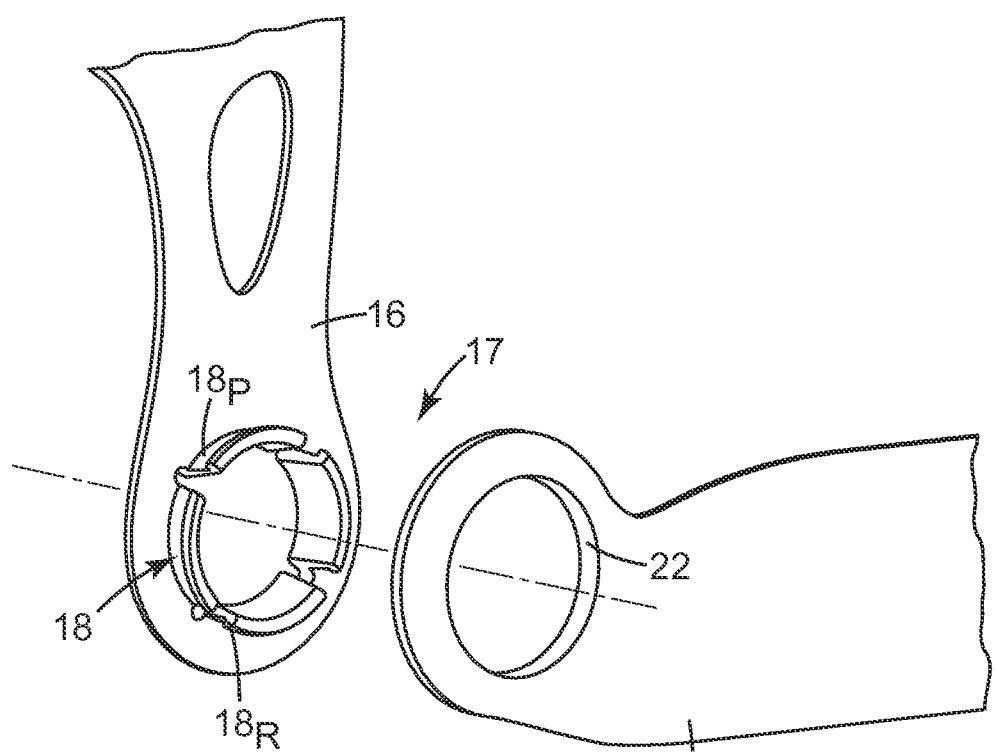
FIG. 7 is a schematic exploded view of the pivot connection shown in FIG. 6.

FIG. 6 is a schematic side elevation view of an illustrative rear support portion 21 and transition arm 16 pivot connection. FIG. 7 is a schematic exploded view of the pivot connection shown in FIG. 6. The transition arm 16 distal end 17 includes the pivot 18. The end of the rear support 21 includes an aperture 22 that is sized to interact with the pivot 18. In many embodiments, the pivot 18 includes one or more projections $18_P$ that provide(s) a snap lock pivot connection with the outer edge of the aperture 22. The outer end of each projection $18_P$ may include one or more ridge(s) $18_R$, which helps secure the rear support aperture 22 to a transition arm 16 distal end 17. Thus, during assembly, the rear support 21 aperture 22 travels over and past the pivot 18 one or more projections $18_P$ and their ridge(s) $18_R$, which flex to allow for insertion into the aperture but subsequently "snaps" together, forming a secure snap lock pivot connection. The ridges $18_R$ are sized such that they overhang the surface forming the aperture 22, preventing the rear support portion 21 and transition arm 16 from separating without inwardly flexing of the pivot 18 projections $18_p$ toward the pivot point 19. Although the figures of the present application show a particular embodiment of the pivot 18, any other suitable configurations are within the scope of the present disclosure. In some embodiments, the pivot 18 is a projection or post extending away from the transition arm 16 major surface. This post can include ridges sized such that they overhang the surface forming the aperture 22, preventing the rear support portion 21 and transition arm 16 from separating without inwardly flexing of the pivot projections toward the pivot point.

In exemplary embodiments, the rear support portion 21 can be attached and detached from the transition arm 16 pivot 18. In one embodiment, the rear support portion 21 can be asymmetric such that a user can assemble it in a low configuration or assemble it in a high configuration where the rear support portion 21 is rotated 180 degrees (e.g., flipped) and thereby elevated up or down (because of its asymmetrical shape) depending on preference. This asymmetric feature of the rear support portion 21 can be utilized to better fit on different back head shapes or for getting free from other head wear. This asymmetric rear support portion 21 can have an upper and/or lower arcuate edge or outer edge (as shown in FIG. 2 and FIG. 4). The arcuate edge can be facing upward toward the top of the user's head (not shown) or facing downward in an opposite direction (as shown in FIG. 2 and FIG. 4). When the asymmetric rear support portion 21 is assembled in a low configuration, the rear support pivots thorough a first pivot range defined by a rear support raised position and a rear support lowered position (as shown in FIG. 4 and FIG. 5). When the asymmetric rear support portion 21 is assembled in a high configuration, the rear support pivots thorough a second pivot range (not shown) defined by a rear support raised position and a rear support lowered position. In these embodiments, the first pivot range is different that the second pivot range.

Thus, embodiments of the HEAD SUSPENSION HAVING TRANSITION ARMS AND REAR SUPPORT are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A head suspension comprising:
   a headband portion having a length and having a bottom edge;
   at least one top band that extends over a user's head and each major end of which is joined to the headband portion;
   two transition arms, each transition arm coupled to the headband portion and extending away from the headband portion length at an angle greater than zero degrees, and each transition arm having a distal end and a pivot at the distal end, the pivot characterized by a pivot point;
      wherein each transition arm comprises a transition arm axis and wherein each transition arm comprises a length in a range from 2 cm to 10 cm, the length being defined by the linear distance, along the transition arm axis of the transition arm, between the bottom edge of the headband portion and the pivot point;
   a rear support portion detachably connected to each pivot, wherein the rear support portion is asymmetric such that a user can detach the rear support portion, rotate the rear support portion 180 degrees, and reattach the rear support portion to each pivot to assemble it in a low configuration or in a high configuration, wherein the headband portion defines a headband plane, wherein the rear support portion is pivotable through a pivot range between a maximum raised position and a maximum lowered position, and wherein the rear support portion is below the headband plane even when the rear support portion is in the maximum raised position; and
   a head protection element attached to the head suspension, wherein the head suspension is configured to support the entirety of the head protection element.

2. A head suspension according to claim 1, wherein each transition arm extends away from the headband portion length at an angle in a range from 20 to 110 degrees.

3. A head suspension according to claim 1, wherein each transition arm extends away from the headband portion length at an angle in a range from 60 to 100 degrees.

4. A head suspension according to claim 1, wherein the rear support portion comprises an adjustment mechanism configured to adjust a length of the rear support portion.

5. A head suspension according to claim 1, wherein the rear support portion comprises a ratchet-type adjustment mechanism configured to adjust a length of the rear support portion.

6. A head suspension according to claim 1, wherein the headband portion is configured to be disposed against a forehead of a user and the rear support portion is configured to be disposed against or below an occipital bone region of a user.

7. A head suspension according to claim 4, wherein the headband portion is configured to be disposed against a forehead of a user and the rear support portion is pivotally disposed in line with an ear canal of a user and below an ear canal of a user.

8. A head suspension according to claim 1, wherein the headband portion is configured to be disposed against a forehead of a user and each pivot point is configured to be disposed below a BL-9 and GB-19 skull pressure points of a user.

9. A head suspension according to claim 1, wherein the head suspension system comprises at least two top bands, each of which top bands extends over the head of a user and each end of which is connected to the headband portion at a location that is proximal to a head protection attachment element of the head suspension.

10. A head suspension according to claim 1, wherein the rear support portion pivotally couples to each pivot by a snap lock.

11. A head suspension according to claim 9, wherein the at least two top bands are non-intersecting with each other.

12. A head suspension according to claim 11, wherein each end of each top band is non-pivotably connected to the headband portion.

13. A head protection device according to claim 1, wherein the head protection element is a welding helmet.

14. A head suspension according to claim 1, wherein each transition arm is integrally formed with the headband portion.

15. A head suspension according to claim 1, wherein each transition arm comprises at least two through-openings, one of which through-openings coincides with the pivot point of that transition arm.

16. A head suspension according to claim 15, wherein the through-opening that coincides with the pivot point of that transition arm is at least partially circumferentially surrounded by at least one projection that protrudes from that transition arm and that at least partially defines the through-opening, and that is insertable into a through-aperture in the rear support portion to form a snap lock that pivotably couples the rear support portion to that transition arm.

17. A head suspension according to claim 16, wherein the at least one projection comprises a ridge that extends generally radially outward from the at least one projection; and, wherein the ridge at least partially overhangs a surface of the rear support portion that at least partially defines the through-aperture in the rear support portion, when the rear support portion is snap-locked to the transition arm.

* * * * *